United States Patent
Xi et al.

(10) Patent No.: US 11,230,693 B2
(45) Date of Patent: Jan. 25, 2022

(54) METHODS FOR HARVESTING MICROALGAE

(71) Applicant: SHENZHEN QIANHAI XIAOZAO TECHNOLOGY CO., LTD., Shenzhen (CN)

(72) Inventors: Weifang Xi, Shenzhen (CN); Wei Yu, Shenzhen (CN); Hongjia Zhang, Shenzhen (CN)

(73) Assignee: SHENZHEN QIANHAI XIAOZAO TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 16/630,602

(22) PCT Filed: Jul. 25, 2017

(86) PCT No.: PCT/CN2017/094260
§ 371 (c)(1),
(2) Date: Jan. 13, 2020

(87) PCT Pub. No.: WO2019/019005
PCT Pub. Date: Jan. 31, 2019

(65) Prior Publication Data
US 2020/0181563 A1    Jun. 11, 2020

(51) Int. Cl.
*C12N 1/12* (2006.01)
*C12P 7/64* (2006.01)

(52) U.S. Cl.
CPC .............. *C12N 1/12* (2013.01); *C12P 7/6436* (2013.01); *C12P 7/6472* (2013.01)

(58) Field of Classification Search
CPC ......... C12N 1/12; C12P 7/6436; C12P 7/6472
See application file for complete search history.

(56) References Cited

FOREIGN PATENT DOCUMENTS

| CN | 101962618 A | | 2/2011 |
|---|---|---|---|
| CN | 104342373 A | | 2/2015 |
| CN | 105624042 A | * | 6/2016 |

OTHER PUBLICATIONS

Yamasaki, S. et al. Effect of dissolved inorganic carbon concentration on oxygen production of a unicellular alga *Nannochloropsis oculata*. Fisheries Science. 2001. 67: 533-534. (Year: 2001).*
Renaud, S. et al. Effect of temperature on growth, chemical composition and fatty acid composition of tropical Australian microalgae grown in batch cultures. Aquaculture. 2002. pp. 195-214 (Year: 2002).*
Hu, H., Gao K. Response of growth and fatty acid compositions of *Nannochloropsis* sp. to environmental factors under elevated CO2 concentration. Biotechnol Lett. 2006. pp. 987-992. (Year: 2006).*
Qin C. et al. Water-solubility of chitosan and its antimicrobial activity. Carbohydrate Polymers. 2006. pp. 367-374 (Year: 2006).*
Crofcheck C. et al. Influence of Flue Gas Components on the Growth Rate of Chlorella vulgarisand Scenedesmus acutus. Transactions of the American Society of Agricultural and Biological Engineers. 2013. pp. 1421-1429. (Year: 2013).*
Zhu B., et al. Large-scale biodiesel production using flue gas from coal-fired power plants with Nannochloropsis microalgal biomass in open raceway ponds. Bioresource Technology. 2014. pp. 53-59 (Year: 2014).*
Mitra M., et al. Integrated process of two stage cultivation of *Nannochloropsis* sp. For nutraceutically valuable eicosapentaenoic acid along with biodiesel. Bioresource Technology. 2015. pp. 363-369 (Year: 2015).*
Roselet, F. et al. Effects of pH, Salinity, Biomass Concentration, and Algal Organic Matter on Flocculant Efficiency of Synthetic Versus Natural Polymers for Harvesting Microalgae Biomass. Bioenerg. Res. 2017. 10, 427-437 (Year: 2017).*
Divakaran et al., (2002). "Flocculation of algae using chitosan," Journal of Applied Psychology, 14:419-422.
Garzon-Sanabria et al., (2013). "Effect of algogenic organic matter (AOM) and sodium chloride on Nannochloropsis salina flocculation efficiency," Bioresour Technol., 143:231-7.
International Search Report and Written Opinion dated Apr. 26, 2018, for PCT Patent Application No. PCT/CN2017/094260 filed on Jul. 25, 2017, 10 pages.
Shah et al. (2014). "A Comprehensive Overview on Various Method of Harvesting Microalgae According to Indian Perspective," International Journal of Research and Scientific Innovation, available online at <https://www.rsisinternational.org/Issue7/313-317.pdf>, 1(7):313-17.

* cited by examiner

*Primary Examiner* — Blaine Lankford
(74) *Attorney, Agent, or Firm* — Morrison & Foerster LLP (57) ABSTRACT

Methods for harvesting microalgae, comprise providing water containing microalgae, providing flocculant in an amount to form flocs of microalgae when mixed with the water, generating a mixture of the water and the flocculant and separating the flocs from the mixture.

20 Claims, 5 Drawing Sheets

METHODS FOR HARVESTING MICROALGAE

CROSS-REFERENCE TO RELATED APPLICATION

This application is a national stage application under 35 U.S.C. 371 of International Application No. PCT/CN2017/094260, filed Jul. 25, 2017, the disclosure of which is hereby incorporated by reference in its entirety.

STATEMENT REGARDING FEDERALLY-SPONSORED RESEARCH

Not applicable

PARTIES TO A JOINT RESEARCH AGREEMENT

Not applicable

REFERENCE TO A SEQUENCE LISTING SUBMITTED ON A COMPACT DISC

Not applicable

BACKGROUND

The present disclosure relates generally to algaculture, and more specifically to culturing and harvesting microalgae.

Microalgae are unicellular, microscopic algae that produce various carbohydrates, proteins, and lipids useful for numerous industrial, nutritional, and medical/pharmaceutical applications. Microalgae are an important starting material for the production of biofuels, nutritional supplements, and pharmaceuticals. (Available at: www.rsisinternational.org/Issue7/313-317.pdf) A cost-efficient, high-yield and reliable means of producing the algal biomass for these applications is critical to the sustainability of algaculture and production of the above-mentioned materials.

Microalgae are photosynthetic organisms capable of growing in diverse aquatic conditions and can be found or cultured in freshwater, saltwater, and brackish water. While microalgae can thrive in a variety of conditions, cultivation conditions impact their growth rate as well as their lipid, protein, and carbohydrate content. For enhanced growth of the microalgae and optimal protein/carbohydrate/lipid content of the microalgae, specific parameters with respect to nutrient quantity and quality, light, pH, turbulence, salinity and temperature must be carefully maintained. (Available at: www.fao.org/docrep/003/w3732e/w3732e06.htm)

Microalgae can be cultivated both indoors and outdoors, in ponds, raceways or closed containers. Isolation of the microalgae from the liquid culture requires separation and concentration of the microalgae from large amounts of water. This can be accomplished through various means. Flocculation and coagulation cause the single-celled microalgae to clump and serve to increase the particle size of the microalgae to facilitate harvesting. While this step is not always necessary, microalgae clumps or flocs can then be more easily separated from the water through centrifugation, floatation or filtering. (Available at: www.rsisinternational.org/Issue7/313-317.pdf and at www.fao.org/docrep/003/w3732e/w3732e06.htm)

Microalgae used to produce extracts for human consumption require especially stringent culturing and harvesting standards. Particularly when grown outdoors in open systems, microalgae can be prone to contamination by other algal species or opportunistic, microbial organisms such as fungi, molds and bacteria. Furthermore, chemical or foreign material contamination whether from outside sources or from the method itself (e.g., chemical flocculants) also should be carefully monitored and steps taken to minimize such potential sources of contamination.

Further to these considerations, any method for microalgae cultivation and harvesting must also account for its long-term sustainability and economic feasibility. The cultivation and harvesting of high-quality microalgae for use, and particularly for producing extracts for human consumption, requires extensive resource investment. There exists a need in the art for an efficient, cost-effective, and reliable method for cultivation and harvesting of microalgae for use towards the production of algal extracts and nutraceuticals.

BRIEF SUMMARY

The presently claimed method provides a reliable and efficient means of culturing and harvesting microalgae. The method addresses the specific needs of providing cultivation and harvesting conditions that promote optimal growth of the microalgae species of interest and enhance the lipid, protein, and carbohydrate content/composition for application in production of algal extracts and nutraceuticals.

The presently claimed method provides a cost-effective means of harvesting microalgae free from harmful contaminants, such as chemical flocculants, microbial contaminants, or environmental impurities. The method therefore is useful for generating algal biomass that can be processed into microalgae-derived nutraceuticals and other manufactures. The method is cost-effective as it directly utilizes sea water, advantageously repurposes flue gas, and economically recycles the water for re-use in microalgae cultivation. Furthermore, costs are greatly reduced by cultivating microalgae in open vessels whereby oxygen need not be specially provided to support growth and also by flocculation of the microalgae prior to harvesting to more efficiently separate water from the microalgae to allow harvesting. The microalgae provided in the claimed method are capable of producing eicosapentaenoic acid (EPA) across a broad range of temperatures permitting for outdoor culture. In view of these factors, the presently claimed method offers a cost-effective and efficient means of cultivating, isolating and harvesting microalgae by harnessing the benefits of the above-named factors to generate superior quality microalgae at high-yield.

The embodiments described herein meets the needs described in the above section by providing methods for harvesting microalgae by providing water containing microalgae, generating a mixture of the water and flocculant, and separating the flocs from the mixture. In certain embodiments, the flocculant is chitosan. In some embodiments of the above-named aspects, chitosan is provided at a concentration of about 2% of the weight of the microalgae in the mixture.

In some embodiments, the microalgae can produce eicosapentaenoic acid (EPA) at temperatures above 32° C. In certain embodiments, the microalgae is *Nannochloropsis*.

In certain embodiments, the water has pH between about 8.0 and about 9.0. In some embodiments, the water has salinity of about 2.2%. In certain embodiments, the water has sodium hydrogen carbonate at a concentration between about 0.1 g/L and about 0.2 g/L. In some embodiments, the water is at a temperature between about 10° C. and about 38° C.

In certain embodiments, the method further comprises adding flue gas or mixing the water with flue gas. In some embodiments, the flue gas has between about 10% and about 14% carbon dioxide. In some embodiments, the flue gas has less than 5 ppm of sulfur dioxide. In certain embodiments, the mixture of the water and flocculant is acidic. In some embodiments, the mixture has a pH of about 5.5.

Certain aspects of the present disclosure relate to methods of preparing a crude microalgal extract. Other aspects of the present disclosure relate to methods of preparing a microalgal lipid extract.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Definitions

The term "flocculant" as used herein refers to an agent that causes aggregation of particles. Flocculant can describe an agent that causes clumping of microalgae to form a microalgae slurry or flocs.

The term "microalgae" as used herein refers to microscopic, unicellular algae.

The term "flue gas" as used herein refers to gas that is released from a flue. Flue gas includes exhaust gas produced by power plants or factories.

Methods of Harvesting Microalgae

The present disclosure relates to a method of harvesting microalgae by providing water containing microalgae, providing an amount of flocculant sufficient to form flocs of microalgae when mixed with water, generating a mixture of the water and flocculant, wherein the mixture is acidic, and separating the flocs from the mixture, thereby harvesting the microalgae.

In certain embodiments, the water is saltwater, freshwater, or brackish water. In other embodiments, the water is seawater. In a preferred embodiment, the water is pumped from the ocean.

In certain embodiments, the water has a pH between about 6.0 and about 10.0. In other embodiments, the water has a pH between about 6.0 and about 6.5, about 6.5 and about 7.0, about 7.0 and about 7.5, about 7.5 and about 8.0, about 8.0 and about 8.5, about 8.5 and about 9.0, about 9.0 and about 9.5, or about 9.5 and about 10.0. In certain embodiments, the water has a pH of about 6.0, about 6.5, about 7.0, about 7.5, about 8.0, about 8.5, about 9.0, about 9.5, or about 10.0. In a preferred embodiment, the water has a pH between about 8.0 and about 9.0.

In certain embodiments, the water has a salinity between about 0.01% and about 5%. In other embodiments, the water has a salinity between about 0.01% and about 0.5%, about 0.5% and about 1.0%, about 1.0% and about 1.5%, about 1.5% and about 2.0%, about 2.0% and about 2.5%, about 2.5% and about 3.0%, about 3.0% and about 3.5%, about 3.5% and about 4.0%, about 4.0% and about 4.5%, or about 4.5% and about 5.0%. In a preferred embodiment, the water has a salinity of about 2.2%.

In certain embodiments, the water comprises sodium hydrogen carbonate at a concentration between about 0.01 g/L and about 0.5 g/L. In some embodiments, the water comprises sodium hydrogen carbonate at a concentration between about 0.01 g/L and about 0.05 g/L, about 0.5 g/L and about 1.0 g/L, about 1.0 g/L and about 1.5 g/L, about 1.5 g/L and about 2.0 g/L, about 2.0 g/L and about 2.5 g/L, about 2.5 g/L and about 3.0 g/L, about 3.0 g/L and about 3.5 g/L, about 3.5 g/L and about 4.0 g/L, about 4.0 g/L and about 4.5 g/L, or about 4.5 g/L and about 5.0 g/L. In a preferred embodiment, the water comprises sodium hydrogen carbonate at a concentration between about 0.1 g/L and about 0.2 g/L.

In certain embodiments, the flocculant is a polysaccharide that forms cationic polyelectrolytes to precipitate the microalgae. In some embodiments, the flocculant is non-toxic. In other embodiments, the flocculant is derived from crustaceans. In yet other embodiments, the flocculant is chitosan. In certain embodiments, the chitosan is provided at a concentration between about 0.08% and about 3.5% of the weight of the microalgae in the mixture. In other embodiments, the chitosan is provided at a concentration between about 0.08% and about 0.5%, about 0.5% and about 1.0%, about 1.0% and about 1.5%, about 1.5% and about 2.0%, about 2.0% and about 2.5%, about 2.5% and about 3.0%, or about 3.0% and about 3.5% of the weight of the microalgae in the mixture. In a preferred embodiment, the chitosan is provided at about 2% of the weight of the microalgae in the mixture.

In certain embodiments, the method comprises adding flue gas or the water is mixed with flue gas. In certain embodiments, the flue gas comprises carbon dioxide. In certain embodiments, the flue gas comprises carbon dioxide at a concentration between about 4% and about 20%. In certain embodiments, the flue gas comprises carbon dioxide at a concentration between about 4% and about 8%, about 8% and about 12%, about 12% and about 16%, or about 16% and about 20%. In other embodiments, the flue gas comprises carbon dioxide at a concentration between about 6% and about 10%, about 10% and about 14%, or about 14% and about 18%. In a preferred embodiment, the flue gas comprises carbon dioxide at a concentration between about 10% and about 14%. In certain embodiments, the flue gas has less than 10 ppm, 9 ppm, 8 ppm, 7 ppm, 6 ppm, 5 ppm, 4 ppm, 3 ppm, 2 ppm, or 1 ppm of sulfur dioxide. In a preferred embodiment, the flue gas has less than 5 ppm of sulfur oxide.

In certain embodiments, the mixture is acidic. In certain embodiments, the mixture has a pH between about 4.5 and about 6.5. In some embodiments, the mixture has a pH between about 4.5 and about 5.0, about 5.0 and about 5.5, about 5.5 and about 6.0, or about 6.0 and about 6.5. In a preferred embodiment, the mixture has a pH of about 5.5.

In certain embodiments, the water containing the microalgae is at a temperature between about 10° C. and about 38°

C. In other embodiments, the water is at a temperature between about 10° C. and about 15° C., about 15° C. and about 20° C., about 20° C. and about 25° C., about 25° C. and about 30° C., about 30° C. and about 35° C., or about 35° C. and about 38° C.

In certain embodiments, after most of the water is drained for recycle use, 15% of the flocs plus remaining water is left in the harvest ponds. In other embodiments, 10% of the flocs plus remaining water or 5% of the flocs plus remaining water is left in the harvest ponds. In a preferred embodiment, 2% of the flocs plus remaining water is left in the harvest ponds.

In certain embodiments, centrifuging the flocs and remaining water is at a separation coefficient between about 1800 and about 3500. In a preferred embodiment, centrifuging the flocs and remaining water is at a separation coefficient of about 2100. In some embodiments, the flocs contain about 10% dry algae weight (i.e., 100 g/L). In other embodiments, the flocs contain 1-2% dry algae weight (i.e., 10 g-20 g/L) or less than 1% dry algae weight (i.e., less than 10 g/L).

In certain embodiments, the microalgae has a high oil content (>20%). In other embodiments, the microalgae comprises 10%, 15%, 20%, 25%, 30%, or 35% polyunsaturated fatty acids. In certain embodiments, the microalgae can produce eicosapentaenoic acid (EPA) at temperatures above 32° C. In certain embodiments, the microalgae can produce >1%, >2%, >3%, >4%, >5%, >6%, >7%, >8%, >9%, >10%, >11%, >12%, >13%, >14%, or >15% EPA.

In certain embodiments, the microalgae is a marine microalgae. In one aspect of the above-named embodiment, the microalgae can grow in seawater provided directly from the ocean. In other embodiments, the microalgae is a freshwater or brackish water microalgae. In other embodiments, the microalgae exist as single cells, as groups, or in chains. In other embodiments, the microalgae is *Isochrysis* sp., *Pseudoisochrysis* sp., *Dicrateria* sp., *Monochrysis* sp., *Tetraselmis* sp., *Pyramimonas* sp., *Micromonas* sp., *Chroomonas* sp., *Cryptomonas* sp., *Rhodomonas* sp., *Chlamydomonas* sp., *Chlorococcum* sp., *Olisthodiscus* sp., *Carteria* sp., *Dunaliella* sp., *Spirulina* sp., *Haematococcus* sp., *Rhodella* sp., *Arthrospira maxima*, or *Nannochloropsis* sp. In a preferred embodiment, the microalgae is *Nannochloropsis* sp. In certain embodiments, the microalgae is *Nannochloropsis gaditana, Nannochloropsis granulate, Nannochloropsis limnetica, Nannochloropsis oceanica, Nannochloropsis oculata,* or *Nannochloropsis salina*. In some embodiments, the *Nannochloropsis* may comprise genetic differences from wild-type *Nannochloropsis* or *Nannochloropsis* found in nature.

Other Methods of the Disclosure

The present disclosure also relates to a method of preparing a crude microalgal extract by providing water containing microalgae, providing an amount of flocculant sufficient to form flocs of microalgae when mixed with water, generating a mixture of the water and flocculant, wherein the mixture is acidic, and separating the flocs from the mixture, thereby preparing a crude microalgal extract.

The present disclosure further relates to a method of preparing a microalgal lipid extract by providing water containing microalgae, providing an amount of flocculant sufficient to form flocs of microalgae when mixed with water, generating a mixture of the water and flocculant under conditions sufficient to form flocs of microalgae, separating the flocs from the mixture, thereby harvesting the microalgae, and extracting lipid from the microalgae, thereby preparing a microalgal lipid extract.

Embodiments of these methods are as described above for the method of harvesting of microalgae.

EXAMPLES

Example 1: Indoor Cultivation 1.1 Purification Process

*Nannochloropsis* sp. was collected in nature and then purified via a simple plating method, by which a single colony with only one microalgae strain in it is formed. Here is an example of preparing 1 Liter media to make agar plate. First 100 ml of each stock solution was prepared as follows:

TABLE 1

Stock Solutions

| Stock solution (100 ml) | Mass (g) |
| --- | --- |
| $MgSO_4 \cdot 7H_2O$ | 24.4 |
| KCl | 6 |
| Urea | 2.5 |
| $CaCl_2 \cdot 2H_2O$ | 3 |
| $KH_2PO_4 \cdot H_2O$ | 0.35 |
| $NaHCO_3$ | 10 |

22 g of NaCl and 15 g of Agar powder were added into 800 ml di H2O, then each stock solution was added as follows. Note that final concentration in the following table is calculated based on each compound in 1 Liter media

TABLE 2

Agar Plate Media

| Compound | Volume | Final concentration (g/L) |
| --- | --- | --- |
| NaCl | / | 22 |
| $MgSO_4 \cdot 7H_2O$ | 10 ml | 2.44 |
| KCl | 10 ml | 0.6 |
| Urea | 10 ml | 0.25 |
| $CaCl_2 \cdot 2H_2O$ | 10 ml | 0.3 |
| $KH_2PO_4 \cdot H_2O$ | 10 ml | 0.035 |
| $NaHCO_3$ | 2 ml | 0.2 |
| P-IV solution | 1 ml | Please refer to Table 3 |
| Agar | / | 15 |

P-IV solution was prepared as follows. Note that the concentration is final to 1 L media

TABLE 3

P-IV Solution

| Compound | Stock solution concentration (g/L) | Final concentration (mg/L) |
| --- | --- | --- |
| $Na_2EDTA \cdot 2H_2O$ | 0.75 | 0.75 |
| $FeCl_3 \cdot 6H_2O$ | 0.097 | 0.097 |
| $H_3BO_3$ | 0.5 | 0.5 |
| $MnSO_4$ | 1.0 | 1.0 |
| $ZnSO_4$ | 0.05 | 0.05 |
| $CoCl_2 \cdot 6H_2O$ | 0.02 | 0.02 |
| $Na_2MoO_4 \cdot 2H_2O$ | 0.1 | 0.1 | di H2O was added up to 1 L, and then pH was adjusted to 7 using HCl or NaOH. The solution was autoclaved at 115 Celsius degree for 30 minutes. 100 ml of each vitamin stock solution was prepared as follows. Note that final concentration is calculated on each compound in 1 Liter media.

TABLE 4

Vitamin Stock Solutions

| Stock solution (100 ml) | Mass (g) | Final concentration (mg/L) |
|---|---|---|
| Vitamin B1 | 0.0335 | 0.335 |
| Vitamin B7 | 0.0025 | 0.025 |
| Vitamin B12 | 0.0135 | 0.135 |

Before vitamin was added into the media, the vitamin stock solution was filtered with a Millipore filter bottle (Millipore Stericup-GP filter bottle 1000/1000 ml with 0.22 μm polyethersulfone membrane Express pus PER). The media was cooled down to 50-70 Celsius degrees, and 1 ml of each axenic vitamin stock solution was added as indicated in Table 4 during constant shaking. The media was transferred to petri-dishes, and then allowed to condense to solid state. An inoculation loop was dipped in the microalgae solution, and a non-overlapped Z-shaped line was gently drawn on the agar culture. The petri-dishes were closed with lids, and then flipped. The dishes were kept in the incubator at 27 Celsius degree. A single colony was picked with inoculation loop and transferred into cultivation beaker. The composition of media used in the beaker will be discussed in the next section. When algae accumulated in the beaker, the above protocol was repeated. After three times, a single strain was obtained.

1.2 Strain Preservation

After the single strain was collected, it was transferred onto a clean agar petri-dish (please check above section for method of preparation). The lids were closed, the plates were flipped, and saved at 4 Celsius degree.

Under such conditions, algae can typically be stored for half a year. Every three months, the algae from the storage (plates with algae stored at 4 Celsius degree) was plated to activate algae from its hibernation (process in which algae grow and degenerate at a very slow rate). This process awakens the cells and this batch of algae and their lineage could maintain its growth and nutritional productivity afterwards.

Plate storage is very susceptible to contamination. Possible contaminants include a variety of strains of microalgae, cyanobacteria, bacteria, phytoplankton and zooplankton. It is necessary to control contaminants from all possible sources such as inherent foreign strains from the original culture, any incoming microorganisms which are brought in from lab operation, contaminants in the air, contaminants which are alive after sterilization process, etc. The heterogeneity will cause early culture to crash. Therefore, plates were divided into different batches and stored on separate layers in the incubators.

For production purpose, plates were produced from different preserved inoculums, in case that one specific inoculum was contaminated initially without being noticed. Strain preservation protocols were heavily executed throughout the whole production period.

1.3 in-Lab Media Preparation

Before scaling up algae from plates, sufficient media was prepared. Here is an example of preparing 1 Liter media for in-lab culture. First, 100 ml of each stock solution was prepared as follows:

TABLE 5

Stock Solutions

| Stock solution (100 ml) | Mass (g) |
|---|---|
| $MgSO_4 \cdot 7H_2O$ | 24.4 |
| KCl | 6 |
| Urea | 2.5 |
| $CaCl_2 \cdot 2H_2O$ | 3 |
| $KH_2PO_4 \cdot H_2O$ | 0.35 |
| $NaHCO_3$ | 10 |

30 g of NaCl was added into 800 ml di H2O, then each stock solution was added as follows. Note that final concentration in the following table is calculated based on each compound in 1 Liter media

TABLE 6

Growth Media

| Compound | Volume | Final concentration (g/L) |
|---|---|---|
| NaCl | / | 30 |
| $MgSO_4 \cdot 7H_2O$ | 10 ml | 2.44 |
| KCl | 10 ml | 0.6 |
| Urea | 10 ml | 0.25 |
| $CaCl_2 \cdot 2H_2O$ | 10 ml | 0.3 |
| $KH_2PO_4 \cdot H_2O$ | 10 ml | 0.035 |
| $NaHCO_3$ | 2 ml | 0.2 |
| P-IV solution | 1 ml | Please refer to Table 7 |

P-IV solution was prepared as follows. Note that the concentration is the final concentration in 1 L media.

TABLE 7

P-IV Solution

| Compound | Stock solution concentration (g/L) | Final concentration (mg/L) |
|---|---|---|
| $Na_2EDTA \cdot 2H_2O$ | 0.75 | 0.75 |
| $FeCl_3 \cdot 6H_2O$ | 0.097 | 0.097 |
| $H_3BO_3$ | 0.5 | 0.5 |
| $MnSO_4$ | 1.0 | 1.0 |
| $ZnSO_4$ | 0.05 | 0.05 |
| $CoCl_2 \cdot 6H_2O$ | 0.02 | 0.02 |
| $Na_2MoO_4 \cdot 2H_2O$ | 0.1 | 0.1 | di H2O was added up to 1 L, and then pH was adjusted to 7 using HCl or NaOH. The solution was autoclaved at 115 Celsius degree for 30 minutes. 100 ml of each vitamin stock solution was prepared as follows. Note that final concentration is calculated on each compound in 1 Liter media.

TABLE 8

Vitamin Stock Solutions

| Stock solution (100 ml) | Mass (g) | Final concentration (mg/L) |
|---|---|---|
| Vitamin B1 | 0.0335 | 0.335 |
| Vitamin B7 | 0.0025 | 0.025 |
| Vitamin B12 | 0.0135 | 0.135 |

Before vitamin was added into the media, the vitamin stock solution was filtered with a Millipore filter bottle (Stericup-GP filter bottle 1000/1000 ml Express pus PER) with 0.22 μm membrane. During the in-lab cultivation, media was not stored. Fresh media was prepared as needed.

1.4 Lab Scale-Up

Algae was captured from the preserved plates with inoculation loops and then transferred into 125 ml beakers (Nalgene™ Single-Use PETG Erlenmeyer Flasks with Plain Bottom: Sterile with Nalgene™ Vented HDPE Closures for Sterile Single Use Erlenmeyer Flasks). Media was added to the beaker until volume reached 50 ml.

These beakers were stored in an incubator where temperature was kept at 22-24 Celsius degree and spin rate was set at 150 rpm. The light intensity inside incubator was set at 35-45 u mol/m2/s. and a mixed combination of CO2 (1-2% v/v according to pH and cell density in the media) and air at a flow rate of 0.1 m3/hr was constantly pumped into the incubator.

After about a week when optical density at 682 nm in the media reached 0.1, culture was transferred from 125 ml beakers to 500 ml beakers (Nalgene™ Single-Use PETG Erlenmeyer Flasks with Plain Bottom: Sterile with Nalgene™ Vented HDPE Closures for Sterile Single Use Erlenmeyer Flasks) and the large beakers were stored in another incubator which remained at the same condition.

Figure 1:
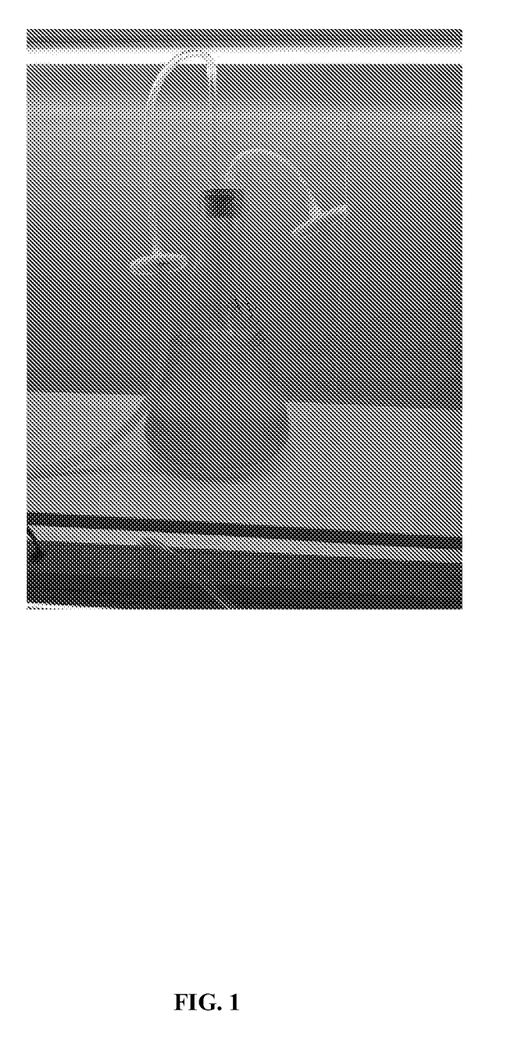
FIG. 1 shows the setup of air pump and filtration design.

After a week, algae was transferred from 500 ml beakers to 5 L glass bottles. Each glass bottle contained 4 L of culture media. These glass bottles were kept on an open bench with a mixed combination of CO2 (1-2% v/v according to pH and cell density in the media) and air at a flow rate of 0.75 L/min was constantly pumped in. FIG. 1 shows the setup of air pump and filtration design. The difference between 5 L glass bottles and smaller beakers in the incubator was that in the glass bottle, air was directly pumped through the rubber stopper and two connected filters (MTGRO5000|Aervent®-50 Filter Unit 0.2 μm hydrophobic ⅛ in. HB/HB), while in the beakers air was firstly pumped into the incubator chamber and then diffused into the media through the vented cap. The glass bottles were manually shaken three times a days, 8 am, 12 pm, 5 pm.

Figure 2:
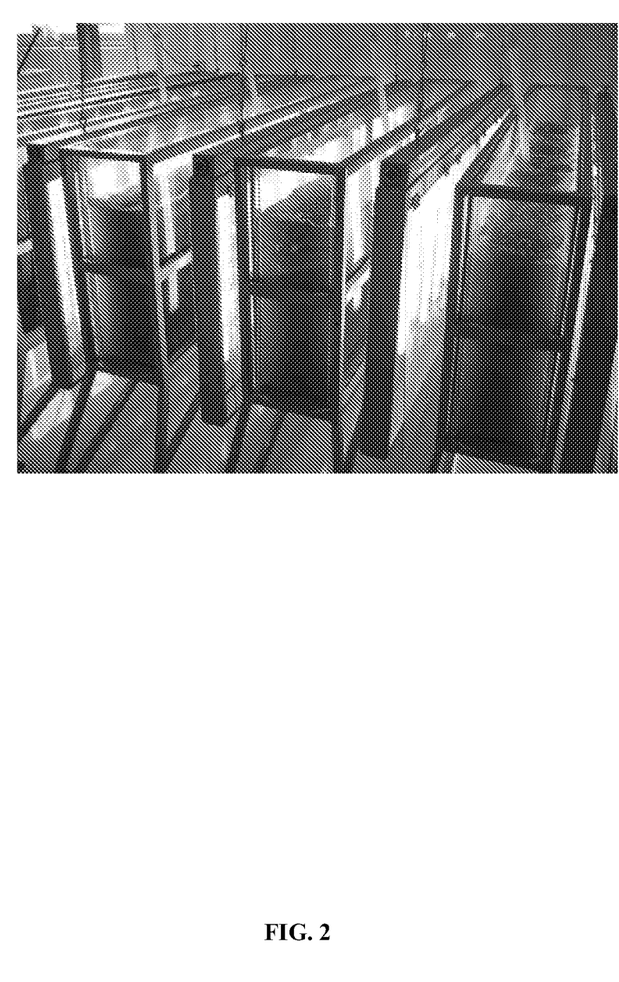
FIG. 2 demonstrates the photo-bioreactor and light panel setup as part of the scale-up process.

After the optical density at 682 nm of algae in the 5 L glass bottles reached 0.3, algae was transferred into 240 L plate photo-bioreactor. These lined photo-bioreactors were made up of glass containers and steel frames attached with mobile wheels on the ground. Light panels which constantly provided light at an intensity of 54-65 μmol/m2/s were hung between each photo-bioreactor. The culture media in the 2 m*0.2 m*0.6 m photo-bioreactors remained at a level of 0.5 m out of total height which equaled 0.6 m. A mixed combination of CO2 (1-2% v/v according to pH and cell density in the media) and air was pumped into each photo-bioreactor at a flow rate of 0.4 m3/hr. Room temperature was kept at 22-24 Celsius degree.

Example 2: Analytic Measurement

2.1 Cell Density Measurement 200 ul algae media was sampled each day for cell density measurement. Samples were loaded onto 96 well plates and absorbance was measured at 682 nm via microplate reader (Molecular Device SpectraMax M2e).

The following relationship was used to evaluate the biomass of our production strain from the optical density measurement Dry Cell Weight=$OD_{682}$*0.687

2.2 Fatty Acid Measurement

The protocol was as follows:

a. 0.1 gram (the figure is accounted to three decimal places) of algae dry powder was weighed into 50 ml centrifuge tubes, and 21 ml of 2:1 chloroform(v)/methanol (v) solution was added. This was shaken on a vortex machine at a rate of 200 r/min for 12 hours.

b. The centrifuge tubes were kept stable until the mixture separated into multi-layers. The supernatant was extracted on the upper layer and transferred into a glass bottle.

c. 21 ml 2:1 chloroform(v)/methanol(v) solution was added to the unfinished centrifuge tubes. They were shaken on a vortex machine at a rate of 200 r/min for 3 hours.

d. Step b was repeated for the centrifuge tubes.

e. All the supernatants were collected in the glass bottle.

f. They were then dried with nitrogen gas. 10 ml 5% (v/v) $H_2SO_4$ methanol solution was added and the bottles were placed in water bath at 100 degrees Celsius for 1 hour.

g. The liquid was allowed to cool down. It was mixed with 2 ml hexane and certain amount of di-$H_2O$. The supernatants were extracted with a syringe and filtered with 0.22 um organic membrane. The filtrate was loaded on gas chromatography (Agilent 7890B) with FID detector which works at a temperature of 280 degrees Celsius.

h. A programmable heater was used from 35° C. (5 min) to 160° C. (0 min) at a rate of 15° C./min, and then from 160° C. (0 min) to 280° C. at a rate of 3° C./min. Sample volume was 0.1 ul.

Below is an analysis measured for total fats, total fatty acids, EPA, and polyunsaturated fatty acids.

TABLE 9

| Measure Date | Algae powder | Total Fats/Algae dry weight by GC (g/100 g) | EPA/Total fatty acids (%) | PUFA/Total Fatty acids (%) |
| --- | --- | --- | --- | --- |
| 2015 Dec. 14 | Nannochloropsis. sp | 21.42 | 32.38 | 41.19 |
| 2015 Dec. 14 | Nannochloropsis. sp | 17.90 | 35.18 | 42.76 |
| 2015 Dec. 30 | Nannochloropsis. sp | 18.44 | 42.03 | 46.85 |

Example 3: Outdoor Cultivation

3.1 Media Preparation

During outdoor cultivation, unpolluted sea water was directly used and pumped from ocean as the media which may significantly reduce costs. Fresh water was firstly used to adjust the salinity to 22 (NaCl/media=22 g/L). Then each component was added (powder was directly poured into ponds) as follows into the media. Any other component was usually not added into sea water except urea and $NaH_2PO_4 \cdot 2H_2O$ since natural formula of sea water was used.

TABLE 9

| Compound | Final concentration (g/L) |
| --- | --- |
| Urea | 0.25 |
| $NaH_2PO_4 \cdot 2H_2O$ | 0.00572 |

3.2 Pond Design

Figure 3:
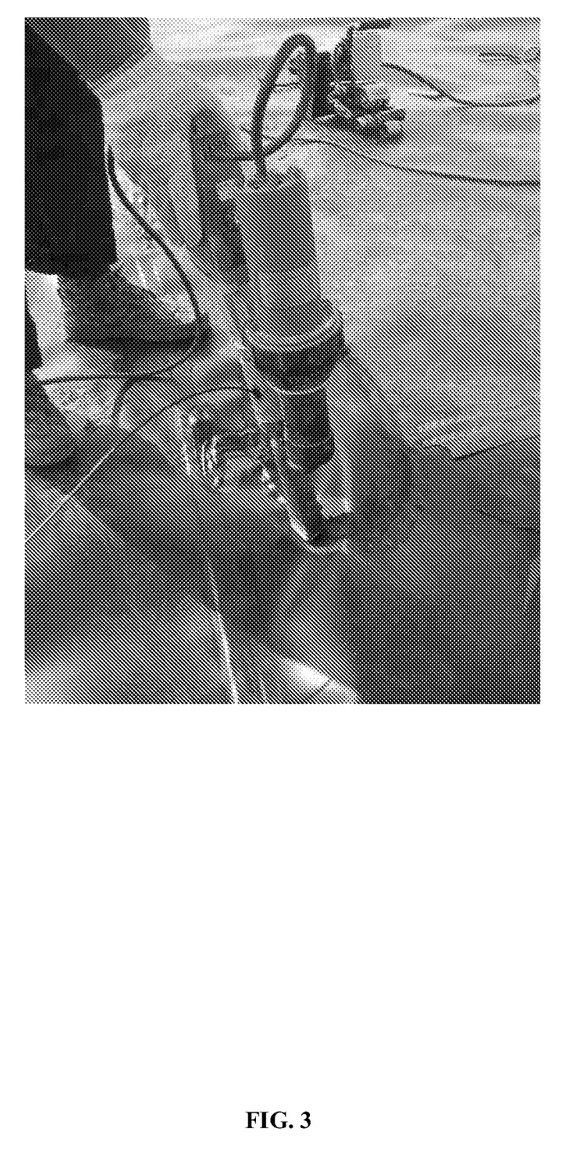
FIG. 3 depicts construction of the outdoor ponds for microalgae cultivation. The ponds are fully lined with HDPE film.

Open raceway ponds were used to scale up microalgae from the indoor plate photo-bioreactors when OD682 in the bioreactors reached 0.4. To construct a pond, a 0.5 m raceway-shaped trench was first dug on the soil ground then covered with HDPE films. Several films were welded to completely cover the pond and the middle ridge without any leakage.

Figure 4:
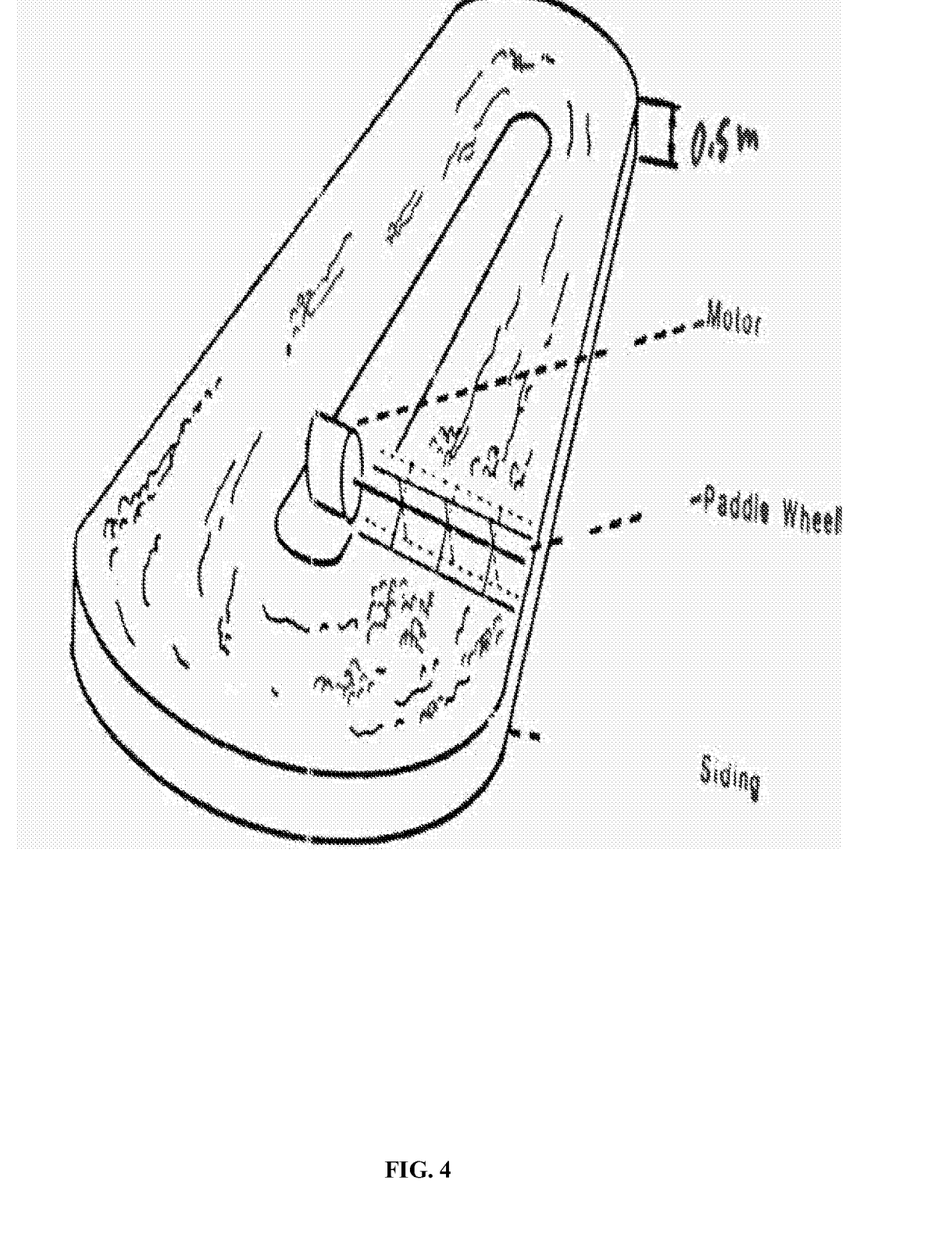
FIG. 4 illustrates the design of the outdoor raceway, including the siding, paddle wheel, and motor.
Figure 5:
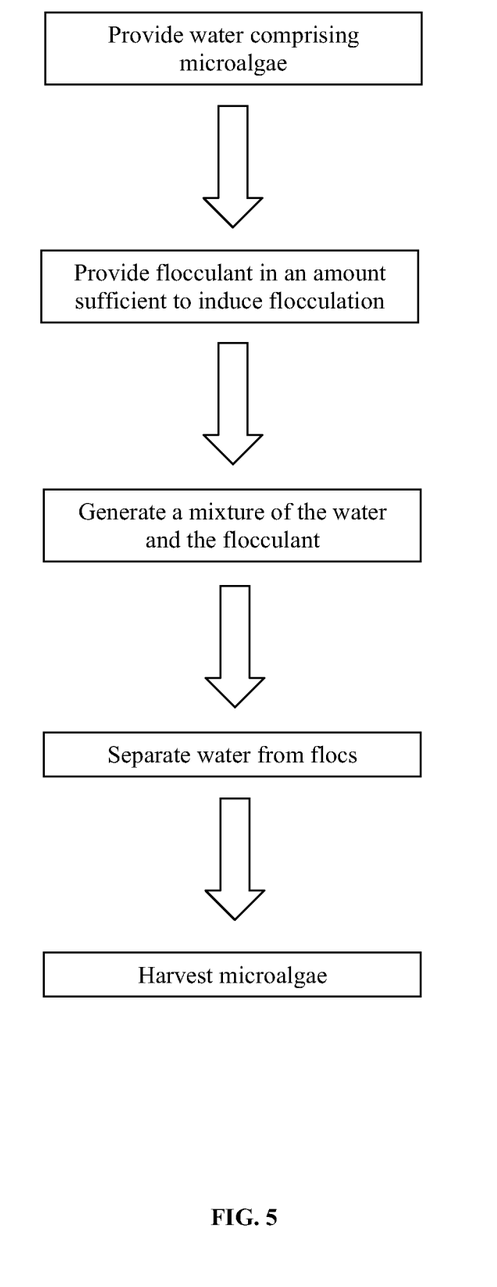
FIG. 5 depicts a flow-chart diagramming the method.

A paddle wheel connected to an electric motor was set between the ridge and the siding of pond. The paddle wheel was constantly rotating so that water and gas was kept circulating in the pond. Gas tubing was set up on selected spots to the bottom of pond. Industrial flue gas which may contain 12-14% (v/v) CO2 was pumped directly into water. Water level in the pond was kept at 30 cm and pH in the water at 7.

3.3 Harvest

For production ponds, all the microalgae was harvested on a weekly basis. All the liquid in the pond was firstly directed/pumped into a harvest pond (usually the harvest pond is much deeper than production pond so it can hold liquid from several production ponds).

Harvest ponds can be designed similar to production ponds with the only difference being that they are much deeper, e.g. 1.2 m depth. When liquid from production ponds flowed into the harvest ponds, the flue gas switch which control in-flow gas to the ponds was turned to maximal so that pH in the ponds would drop below 6. Chitosan stock solution (1% chitosan to the biomass contained in the ponds) was then added as harmless flocculant to induce auto-precipitation. Under acidic solution, it causes microalgae in the water to flocculate.

For example, if 1000 metric tons of liquid were in the harvest ponds and OD682 in it read 0.6, the biomass contained in the ponds was 0.6*0.687*1000*1000=412.2 kg. Therefore 412.2 kg*1%=4.12 kg chitosan was added in the pond.

Chitosan stock solution was prepared by: Adding 0.1 g chitosan powder into 10 ml 0.1M HCl solution then filling with water to 100 ml to reach a final concentration of chitosan in the stock solution equivalent to 1 g/L.

After flocculation, most of the water was directly drained for recycle use and then only leaving around 10% of the flocs plus remaining water in the harvest ponds. The siding of harvest ponds was then washed in order to collect all the flocs which had stuck to the siding of the ponds. These flocs and remaining water were pumped into horizontal centrifuge. Centrifuging them at a separation coefficient of 2100 easily separated the microalgae slurry (over 10% dry algae weight) from the remaining water.

$$\text{Separation coefficient } RCF = \frac{F_{ef}}{G} = \frac{m\omega^2 r}{mg} = \frac{\omega^2 r}{g}$$

Pressure filtration was also used to separate microalgae flocculants from remaining water using 500 meshes membrane (30 um pore size). Microalgae slurry was collected through filtration. The microalgae slurry was fed into spray dryer and dried.

What is claimed is:

1. A method for harvesting microalgae, the method comprising
providing water comprising microalgae,
wherein the water has a pH between about 6.0 and about 10.0 and has a salinity between about 0.01% and about 5%;
providing chitosan in an amount sufficient to form flocs of microalgae when mixed with the water;
generating a mixture of the water and the chitosan, wherein the mixture is acidic; and
separating the flocs from the mixture, thereby harvesting the microalgae.

2. The method of claim 1, wherein the water has a pH between about 8.0 and about 9.0.

3. The method of claim 1, wherein the water has a salinity of about 2.2%.

4. The method of claim 1, wherein the water comprises sodium hydrogen carbonate at a concentration between about 0.01 g/L and about 0.5 g/L.

5. The method of claim 4, wherein the water comprises sodium hydrogen carbonate at a concentration between about 0.1 g/L and about 0.2 g/L.

6. The method of claim 1, wherein the water is at a temperature between about 10° C. and about 38° C.

7. The method of claim 1, wherein the chitosan is provided at a concentration between about 0.08% and about 3.5% of the weight of the microalgae in the mixture.

8. The method of claim 1, wherein the chitosan is provided at about 2% of the weight of the microalgae in the mixture.

9. The method of claim 1, wherein the method comprises adding flue gas or wherein the water is mixed with flue gas.

10. The method of claim 9, wherein the flue gas comprises carbon dioxide.

11. The method of claim 9, wherein the flue gas has less than 5 ppm of sulfur oxide.

12. The method of claim 9, wherein the flue gas comprises carbon dioxide at a concentration between about 4% and about 20%.

13. The method of claim 9, wherein the flue gas comprises carbon dioxide at a concentration between about 10% and about 14%.

14. The method of claim 1, wherein the mixture has a pH between about 4.5 and about 6.5.

15. The method of claim 14, wherein the mixture has a pH of about 5.5.

16. The method of claim 1, wherein the microalgae can produce eicosapentaenoic acid (EPA) at temperatures above 32° C.

17. The method of claim 1, wherein the microalgae is *Nannochloropsis*.

18. A method for preparing a crude microalgal extract, the method comprising
providing water comprising microalgae,
wherein the water has a pH between about 6.0 and about 10.0 and has a salinity between about 0.01% and about 5%;
providing chitosan in an amount sufficient to form flocs of microalgae when mixed with the water;
generating a mixture of the water and the chitosan, wherein the mixture is acidic; and
separating the flocs from the mixture, thereby preparing a crude microalgal extract.

19. A method for preparing a microalgal lipid extract, the method comprising
providing water comprising microalgae,
wherein the water has a pH between about 6.0 and about 10.0 and has a salinity between about 0.01% and about 5%;
providing chitosan in an amount sufficient to form flocs of microalgae when mixed with the water;
generating a mixture of the water and the chitosan, wherein the mixture is acidic;
separating the flocs from the mixture, thereby harvesting the microalgae; and
extracting lipid from the microalgae, thereby preparing a microalgal lipid extract.

20. The method of claim 1, wherein the water has a salinity selected from the group consisting of between about 0.5% and about 1.0%, between about 1.0% and about 1.5%, between about 1.5% and about 2.0%, between about 2.0% and about 2.5%, between about 2.5% and about 3.0%, between about 3.0% and about 3.5%, between about 3.5% and about 4.0%, and between about 4.0% and about 4.5%.

\* \* \* \* \*